United States Patent
Zhang

(10) Patent No.: US 9,964,526 B2
(45) Date of Patent: May 8, 2018

(54) PHASED-ARRAY PROBE AND A PHASED-ARRAY SEARCH UNIT

(71) Applicant: Jinchi Zhang, Quebec (CA)

(72) Inventor: Jinchi Zhang, Quebec (CA)

(73) Assignee: Olympus Scientific Solutions Americas Inc., Waltham, MA (US)

( * ) Notice: Subject to any disclaimer, the term of this patent is extended or adjusted under 35 U.S.C. 154(b) by 212 days.

(21) Appl. No.: 15/086,200

(22) Filed: Mar. 31, 2016

(65) Prior Publication Data
US 2016/0290973 A1    Oct. 6, 2016

Related U.S. Application Data

(60) Provisional application No. 62/140,962, filed on Mar. 31, 2015.

(51) Int. Cl.
  *G01N 29/04*   (2006.01)
  *G01N 29/24*   (2006.01)
  *G01N 29/26*   (2006.01)
  *G01N 29/32*   (2006.01)

(52) U.S. Cl.
  CPC ........... *G01N 29/32* (2013.01); *G01N 29/043* (2013.01); *G01N 29/2487* (2013.01); *G01N 29/262* (2013.01); *G01N 2291/044* (2013.01); *G01N 2291/106* (2013.01); *G01N 2291/2632* (2013.01); *G01N 2291/2634* (2013.01)

(58) Field of Classification Search
  CPC .. G01N 29/32; G01N 29/043; G01N 29/2487; G01N 29/262; G01N 2291/2634; G01N 2291/044; G01N 2291/106; G01N 2291/2632

USPC .......................................................... 73/628
See application file for complete search history.

(56) References Cited

U.S. PATENT DOCUMENTS

| | | | | |
|---|---|---|---|---|
| 4,680,967 A | * | 7/1987 | Rost | G01N 29/28 310/336 |
| 8,756,999 B2 | * | 6/2014 | Graff | G01N 29/2487 73/632 |
| 8,770,027 B2 | * | 7/2014 | Oberdoerfer | G01N 29/07 73/597 |
| 9,110,000 B2 | * | 8/2015 | Poirier | G01N 29/069 |
| 2013/0312528 A1 | * | 11/2013 | Feydo | G01N 29/262 73/632 |
| 2015/0233869 A1 | * | 8/2015 | Barrett | G01N 29/043 376/249 |

* cited by examiner

*Primary Examiner* — J M Saint Surin
(74) *Attorney, Agent, or Firm* — C. Tricia Liu

(57) ABSTRACT

The phased-array probe to be received on a probe receiving area of a wedge generally has a probe housing, a plurality of acoustic transducer elements disposed in the probe housing and distributed along a length of a working surface of the probe housing, and a matching layer covering the plurality of acoustic transducer elements and extending to cover an extended region of the working surface of the probe housing such that the matching layer forms a closed contact with an upper end of an acoustic damping junction of the wedge when the working surface of the probe housing of the phased-array probe is received on the probe receiving area of the wedge, wherein the closed contact prevents acoustic energy from being reflected from the extended region of the working surface of the probe housing.

19 Claims, 4 Drawing Sheets

PHASED-ARRAY PROBE AND A PHASED-ARRAY SEARCH UNIT

CROSS-REFERENCE TO RELATED APPLICATIONS

This application claims the benefit and priority of U.S. provisional patent application Ser. No. 62/140,962 filed Mar. 31, 2015 entitled A PHASED-ARRAY PROBE AND A PHASED-ARRAY SEARCH UNIT, the entire disclosure of which is incorporated herein by reference.

FIELD

The improvements generally relate to the field of nondestructive testing (NDT) and more particularly to the field of phased-array ultrasonic testing (PAUT).

BACKGROUND

For years now, ultrasonic waves (i.e. high frequency acoustic waves) have been used to detect cracks, voids, porosity, and other internal discontinuities hidden in solid material such as metals, composites, plastics, and ceramics, as well as to measure thickness and analyze solid material properties. For instance, phased-array (PA) ultrasonic testing is an inspection technique which is known to be nondestructive, safe and, by now, well-established in the manufacturing, process, and service industries.

Phased-array ultrasonic testing involves the use of a search unit, typically including a conventional PA probe mounted on a conventional wedge, for propagating acoustic signals in a part to inspect and for detecting echoes of the acoustic signals within the part in order to localize and size flaws that may or may not exist in the inspected part.

During use, acoustic transducer elements of the conventional PA probe propagate the acoustic signals within the conventional wedge and through a wedge-probe interface before reaching the part to inspect. As the acoustic signals refract at the wedge-probe interface, some portion of the acoustic signals are generally reflected within the conventional wedge, toward a given larger end of the conventional wedge, which may cause noise if reflected back at any one of the acoustic transducer elements. In order to prevent these undesirable reflected acoustic signals from causing additional noise in the measurements, the conventional wedge generally has an acoustic damping structure at the given larger end for damping the undesirable reflections before they reach any one of the acoustic transducer elements. Although existing search units are satisfactory to a certain degree, there remains room for improvement.

SUMMARY

It was found that when the undesirable reflected acoustic signals are propagated toward the larger end of the conventional wedge and toward the acoustic damping structure, not all the undesirable reflected acoustic signals are damped by the acoustic damping structure. Moreover, it was found that a portion of the undesirable reflected acoustic signals typically reach a front portion of the conventional PA probe. However, the front portion of the conventional PA probe has a given amount of acoustic discontinuities, i.e. abrupt changes in impedance, which can cause the portion of the undesirable reflected acoustic signals to be reflected back to any one of the acoustic transducer elements.

In order to at least reduce the undesirable effects of the acoustic discontinuities of the conventional PA probe, there is provided a PA probe and a wedge that reduce the undesirable effects of the acoustic discontinuities of the front portion of the PA probe. Broadly stated, the PA probe has an extended matching layer which, when the PA probe is positioned on a probe receiving area of the wedge, extends and covers not only the acoustic transducer elements but also an upper end of the damping junction of the wedge to form a closed contact with the upper end of the acoustic damping junction in order to prevent acoustic energy from being transmitted over the matching layer and, in turn, from being reflected back from the PA probe toward the acoustic transducer elements.

In accordance with one aspect, there is provided a phased-array probe to be received on a probe receiving area of a wedge, the phased-array probe comprising a probe housing, a plurality of acoustic transducer elements disposed in the probe housing and distributed along a length of a working surface of the probe housing, and a matching layer covering the plurality of acoustic transducer elements and extending to cover an extended region of the working surface of the probe housing such that the matching layer forms a closed contact with an upper end of an acoustic damping junction of the wedge when the working surface of the probe housing of the phased-array probe is received on the probe receiving area of the wedge, wherein the closed contact prevents acoustic energy from being reflected from the extended region of the working surface of the probe housing.

In this aspect, the extended region can include a spacing between a last one of the plurality of acoustic transducer elements and an interior wall of the probe housing adjacent to the last one of the plurality of acoustic transducer elements.

In this aspect, the spacing of the extended region can receive an acoustic discontinuity compensator element having acoustic properties similar to that of the acoustic transducer elements.

In this aspect, the acoustic discontinuity compensator element can be provided in the form of a given acoustic transducer element. In an alternate embodiment, the given acoustic transducer element can be oversized compared to each of the plurality of acoustic transducer elements.

In this aspect, the matching layer can be made of a material having an impedance corresponding to that of a material of the wedge.

In accordance with another aspect, there is provided a phased-array search unit comprising: a wedge having a base, a top inclined surface opposite to the base, the wedge tapering from a larger end to a smaller end of the wedge, the wedge further comprising an acoustic damping structure provided at an acoustic damping junction of the larger end; and a phased-array probe having a probe housing, the housing further having a working surface to be received on the top inclined surface of the wedge; a plurality of acoustic transducer elements forming part of the working surface of the probe housing and distributed along a length of the working surface; and a matching layer covering the plurality of acoustic transducer elements along the length of the working surface of the probe housing; wherein the matching layer and the acoustic damping structure are configured to extend toward each other to form a closed contact so that acoustic energy is substantially blocked from being transmitted beyond at least one of the matching layer and the damping junction.

In this aspect, the acoustic damping junction can extend from the base toward the top inclined surface of the wedge.

The acoustic damping junction can prevent the acoustic energy transmitted from the plurality of acoustic transducer elements via a reflection at the base of the wedge to be reflected back toward the plurality of acoustic transducer elements.

In this aspect, the acoustic damping junction can have an upper end located inward from an interior wall of the probe housing and covered by the matching layer when the working surface of the probe housing is received on the top inclined surface of the wedge.

In this aspect, the acoustic damping junction can have a plurality of spaced apart teeth. The plurality of spaced apart teeth can be sized and shaped to prevent the acoustic energy from being transmitted back toward the plurality of acoustic transducer elements.

In this aspect, the acoustic damping structure can be made of a material for diffusing the acoustic energy.

In this aspect, the matching layer can extend along the length of the working surface in a direction of the larger end of the wedge when the working surface of the probe housing is received on the top inclined surface of the wedge to cover an extended region of the working surface.

In this aspect, the extended region can include a spacing between a last one of the plurality of acoustic transducer elements and a wall of the probe housing adjacent to the last one of the plurality of acoustic transducer elements.

In this aspect, the spacing of the extended region of the base portion can receive an acoustic discontinuity compensator element positioned adjacent to a last one of the plurality of acoustic transducer elements. The acoustic discontinuity compensator element having acoustic properties similar to the acoustic properties of the acoustic transducer elements.

In this aspect, the base can include a planar surface. The base can include a curved surface shaped to be received on a curved part to inspect (e.g., a pipe).

In this aspect, the top inclined surface can include a planar surface having an inclination ranging from 15° to 55° relatively to the base. The top inclined surface can include a curved surface, or any suitable shape for receiving the working surface of the probe housing.

In this aspect, the matching layer can be made of a material having an impedance corresponding to that of a material of the wedge.

In this aspect, the acoustic damping junction can have a curved damping profile grooved from the base of the wedge toward the top inclined surface of the wedge.

In this aspect, the working surface can include a planar surface. The working surface can have a curved surface, or any suitable shape to be received on the top inclined surface of the wedge.

In this aspect, the plurality of acoustic transducer elements can be spaced from one another along the length of the working surface. The acoustic transducer elements can be equally spaced from one another. The acoustic transducer elements can also be abutted on one another.

In accordance with another aspect, there is provided a phased-array search unit comprising: a wedge having a back portion tapering from a front portion of the wedge along a length of the wedge, the back portion having a probe receiving area; and an acoustic damping structure provided at an acoustic damping junction of the front portion of the wedge, the acoustic damping junction extending toward an upper band of the probe receiving area; and a phased-array probe having a probe housing having a base portion to be received on the probe receiving area of the wedge; a plurality of acoustic transducer elements disposed in the probe housing and distributed along a length of the probe housing and at the base portion of the probe housing; and a matching layer covering the plurality of acoustic transducer elements along the length at the base portion of the probe housing, the matching layer extending along the length of the probe housing in a direction of the front portion of the wedge to cover an extended region of the base portion of the probe housing which corresponds to the upper band of the probe receiving area when the phased-array probe is received on the probe receiving area of the wedge.

Many further features and combinations thereof concerning the present improvements will appear to those skilled in the art following a reading of the instant disclosure.

DESCRIPTION OF THE FIGURES

In the figures.

DETAILED DESCRIPTION

Description of the Challenges Addressed in this Disclosure

Figure 1:
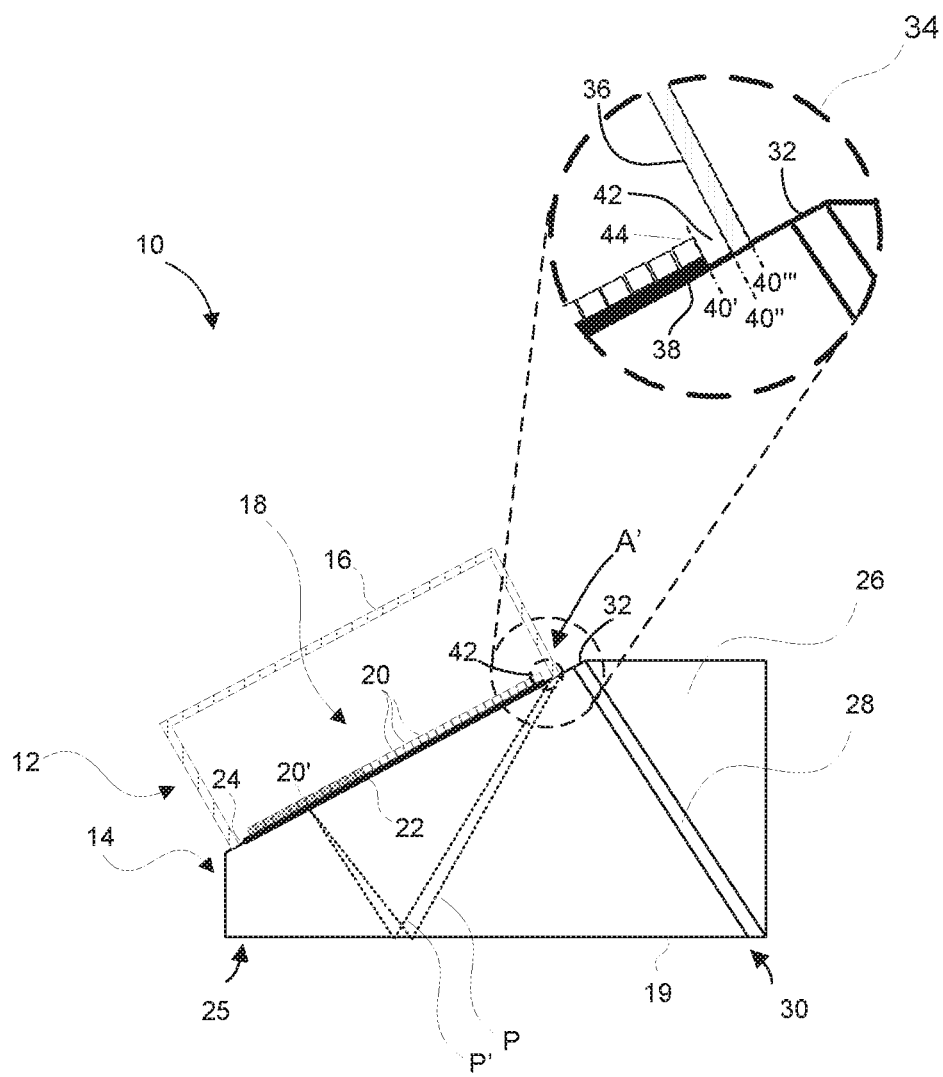
FIG. 1 is a schematic side view of a conventional search unit.

In order to clearly illustrate the above-mentioned acoustic discontinuities that are at least partially addressed in this disclosure, FIG. 1 shows a side view of a conventional search unit 10 including a conventional phased-array (PA) probe 12 and a conventional wedge 14.

The conventional PA probe 12 has a probe housing 16, an array 18 of acoustic transducer elements 20 (also referred to as "active apertures 20") and a matching layer 22 covering the acoustic transducer elements 20. The conventional wedge 14 has a base 19 and an opposite, inclined, top surface 24 disposed on a smaller end 25 thereof for receiving the probe housing 16 as shown in FIG. 1. The conventional wedge 14 has an acoustic damping structure 26 grooved at an acoustic damping junction 28 of a larger end 30 of the conventional wedge 14. The larger end 30 tapers to the smaller end 25 along a length of the conventional wedge 14 such that the top inclined surface 24 is on the smaller end 25 of the conventional wedge 14. As depicted, the acoustic damping junction 28 of the conventional wedge 14 is provided in the form of a saw-tooth junction that extends obliquely in the conventional wedge 14. Typically, a conventional upper end 32 of the acoustic damping junction 26 extends at a position which is spaced from the probe housing 16 of the conventional PA probe 12, as shown in inset 34.

As depicted by acoustic paths P, P', it was found that when a given reflected acoustic signal is reflected toward region A', acoustic discontinuities up along a front portion 36 of the conventional PA probe 12 (see path P) and along the front end 38 of the matching layer 22 (see path P') can cause undesirable reflections within the conventional wedge 14 and thus cause additional noise on the measurements of any of the active apertures 20, for instance.

More specifically, when the conventional PA probe 12 is received on the conventional wedge 14, as shown in FIG. 1, the acoustic discontinuities caused by the discontinuous contacts between the front portion 36 of the probe housing 16 and the top inclined surface 24 in the larger end 30 of the conventional wedge 14 and the discontinuous contact between the front end 38 of the matching layer 22 and the top inclined surface 24 in the larger end 30 of the conventional wedge 14 are exposed to any acoustic beams coming from the inside of the conventional wedge 14. Those acoustic beams can be from any aperture at any working angle in the conventional wedge 14. In the exemplary search unit of the prior art shown in FIG. 1, active aperture 20' detects the undesirable reflections, i.e. wedge noise, caused by the echo of an L-wave reflected on the acoustic discontinuities typically located in region A'.

Such acoustic discontinuities occur in cases where there is an abrupt change of impedance with the material in contact with the top inclined surface 24 of the conventional wedge 14. For instance, the impedance of the material of the matching layer 22 is relatively close to the impedance of the material of the conventional wedge 14 so that no acoustic discontinuity occurs. However, it was found that abrupt changes of impedance can be found at least at a first interface 40' between an adhesive filled region 42 (e.g., epoxy filled) and the adjacent one 44 of the acoustic transducer elements 20, at a second interface 40" between the adhesive filled region 42 and the front portion 36 of the probe housing 16 and at a third interface 40''' between the front portion 36 of the probe housing 16 and the exterior (i.e. the air) of the probe housing 16. Further, the adhesive filled region 42 may not be in suitable contact with the wedge 14 thereby creating a pocket (not shown) filled with couplant (e.g., water, gel etc.). In either case, acoustic discontinuities are likely to occur in region A', as illustrated in FIG. 1.

The above-mentioned acoustic discontinuities can react to any incident beam as a line-like target on the larger end 30 of the conventional wedge 14. Unlike the large discontinuous interface between the conventional PA probe 12 and the conventional wedge 14 during use which reflects incident acoustic signals toward the acoustic damping structure 26 for diffusing acoustic energy, each above line-like discontinuity which is perpendicular to the acoustic incident beams can reflect back the incident beam toward any one of the active apertures 20 of the array 18, thus generating some noise in the measured signal.

Description of Exemplary Embodiments which can Address the Above-Mentioned Challenges FIG. 2A to FIG. 4 show exemplary embodiments of a PA probe 52 and of a wedge 54 in accordance with some embodiments of the present disclosure whereby like elements will bear like reference numerals for ease of reading.

Figure 2A:
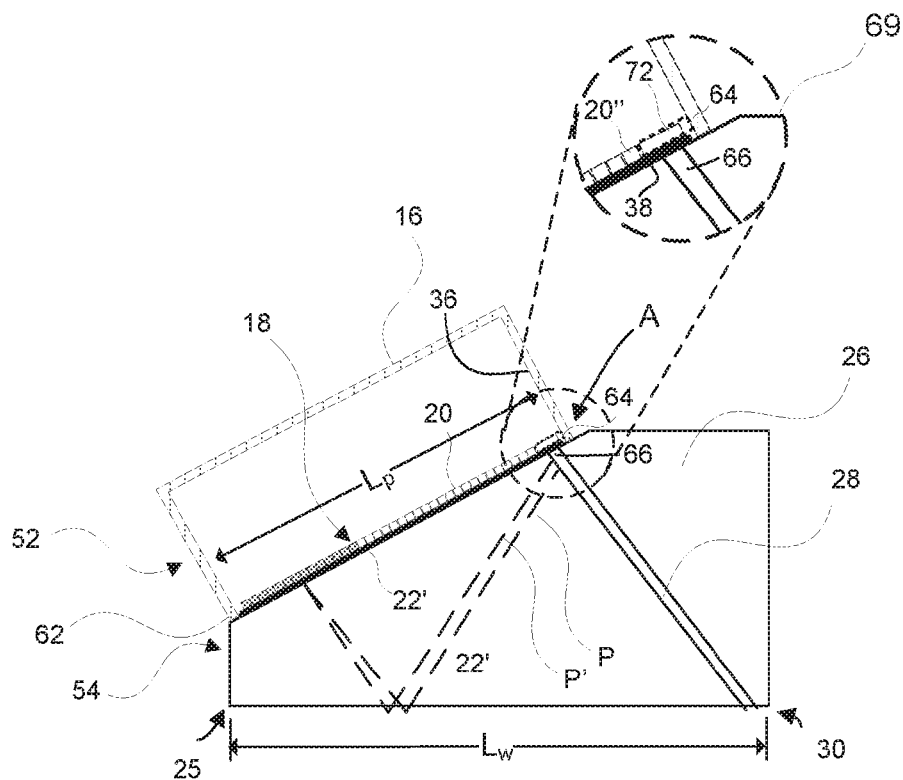
FIG. 2A is a schematic side view of a search unit, in accordance with an embodiment.
Figure 2B:
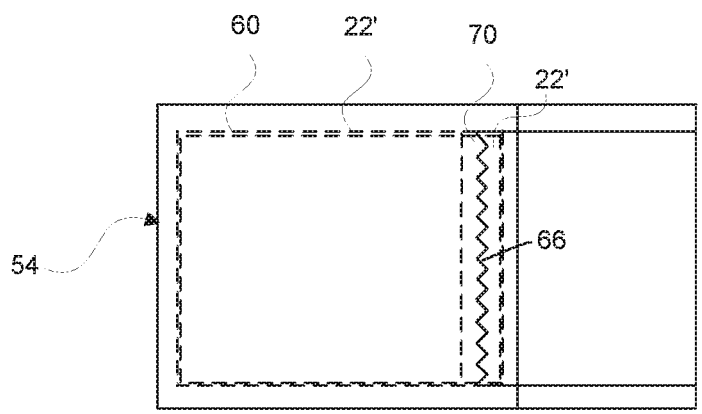
FIG. 2B is a schematic top view of the wedge of FIG. 2A, in accordance with an embodiment.

FIGS. 2A-2B show respectively a side view of the PA probe 52 which is received on a probe receiving area 60 of the wedge 54 and a top view of the wedge 54 shown in FIG. 2B. Referring particularly to FIG. 2A, the PA probe 52 has a probe housing 16 and an array 18 of acoustic transducer elements 20 disposed at a working surface 62 of the probe housing 16 such that, during use, the working surface 62 of the probe of the probe housing 16 is received on the probe receiving area 60 (which is best seen on FIG. 2B) of the wedge 54 to perform phased-array testing. The plurality of acoustic transducer elements 20 is distributed along a length $L_p$ of the working surface 62 of the probe housing 16. The PA probe 52 also has an extended matching layer 22' which covers the plurality of acoustic transducer elements 20 at the working surface 62 of the probe housing 16. The matching layer 22' also extends to cover, not only the acoustic transducer elements 20, but also an extended region 64 of the working surface 62 of the probe housing 16 such that the matching layer 22' covers, during use, an upper end 66 of an acoustic damping junction 28 of the wedge 54 when working surface 62 of the probe housing 16 of the PA probe 52 is received on the probe receiving area 60 of the wedge 54, as best shown in inset 69. Accordingly, the matching layer 22' extends further than a last one of the active apertures 20, i.e. the last active aperture 20" which is adjacent to the extended region 64), to cover the extended region 64. Moreover, the oblique angle of the acoustic damping junction 28 is chosen so that, during use, the front portion 36 (can also be referred to as an interior wall) of the probe housing 16 and the front end 38 of the matching layer 22' are covered by the acoustic damping junction 28 if viewed from the inside of the wedge body.

By providing such a structure, during use, the extended matching layer 22' and the upper end 66 of the acoustic damping junction 28 form a closed contact which can prevent (or substantially block) acoustic energy from being transmitted over the extended matching layer 22' and, in turn, from being reflected from the front portion 36 of the PA probe 52 back toward the acoustic transducer elements 20. Thus, most of the sound beams originating from any and all elements 20 are stopped at the acoustic damping junction 28, before reaching the front portion 36 of the probe housing 16 and the front end 38 of the extended matching layer 22', at which acoustic discontinuity could have occurred.

By providing such an extended matching layer 22', there is provided a homogeneous and uniform surface in contact with the wedge 54 which has a constant impedance (no abrupt changes of impedance) and that is in contact force (no couplant pocket) with the wedge in order to reduce the acoustic discontinuities. The extended matching layer 22' creates a uniform and continuous contact (as opposed to discontinuous contact) along an entire length of the working surface 62 of the PA probe 52 and beyond the upper end 66 of the acoustic damping junction 28. Moreover, the PA probe 52 and wedge 54, when mounted in an inspection position, allow for preventing undesirable reflected acoustic signals to be reflected from region A of the probe housing 16, as shown in FIG. 2A. In other words, the upper end 66 of the acoustic damping junction 28 extends from a bottom portion of the wedge 54 toward an upper band 70 of the probe receiving area 60 so that the front portion 36 of the probe housing 16 is hidden from undesirable reflected acoustic signals with the acoustic damping junction 28.

As best shown in the inset 69, the PA probe 52 also has an optional acoustic discontinuity compensator element 72 (also referred to as "dumb element 72") positioned at the extended region 64 located in the front portion 36 of the probe housing 16 in order to be covered by the extended matching layer 22'. The dumb element 72 is used to keep acoustic continuity of the contact between the extended matching layer 22' and the inclined, top inclined surface 24 beyond the last active aperture 20". It is noted that the dumb element 72 has acoustic properties similar to the acoustic properties of the active apertures to avoid acoustic discontinuities along the bottom portion of the PA probe 52. For instance, the dumb element can be made of the same material as the transducer elements 20 of the array 18 and is placed adjacent to the last active aperture 20" near the front portion 36 of the probe housing 16. In the embodiment shown in FIG. 2A, the dumb element 72 is oversized compared to the other transducer elements 20 of the array 18. The size of the dumb element 72 can vary depending of the depth of the grooves of the acoustic damping junction 28, for instance.

In another embodiment, the dumb element 72 is provided in the form of a plurality of smaller dumb elements. In a further embodiment, the dumb element 72 is an active aperture which is not used during inspection. In a still further embodiment, the dumb element 72 can be replaced by any material such as a kind of epoxy that can help to keep continuous contact between the PA probe 52 and the top inclined surface 24 of the wedge 54.

As shown, the wedge 54 tapers from the larger end 30 along a length $L_w$ such that the larger end 30 has a greater thickness than the smaller end 25 of the wedge 54. The acoustic damping junction 28 extends obliquely from the bottom portion of the wedge 54 toward the upper band 70 of the probe receiving area 60 in order to prevent undesirable reflected acoustic signals from reaching the acoustic discontinuity of the front portion 36 of the PA probe 52. As shown in FIG. 2A, acoustic paths P, P' show that the path of wedge noise that is intercepted by the acoustic damping junction 28 of the wedge 54, which was not the case when using the conventional wedge 14 shown in FIG. 1. Referring back to FIG. 2A, the paths of potential undesirable reflected acoustic signals heading toward region A of the probe housing 16 and toward the extended matching layer 22' are cut by the acoustic damping junction 28 at a location beneath the extended region 64, or beneath the dumb element 72.

Still referring to FIG. 2A, the acoustic damping junction 28 has a uniform surface (no abrupt changes of direction) from the base portion of the wedge 54 up to the probe receiving area 60. This uniform surface is preferred in order to avoid creating sources of noise that occur when a "corner" is created between two adjacent surfaces.

Figure 3:
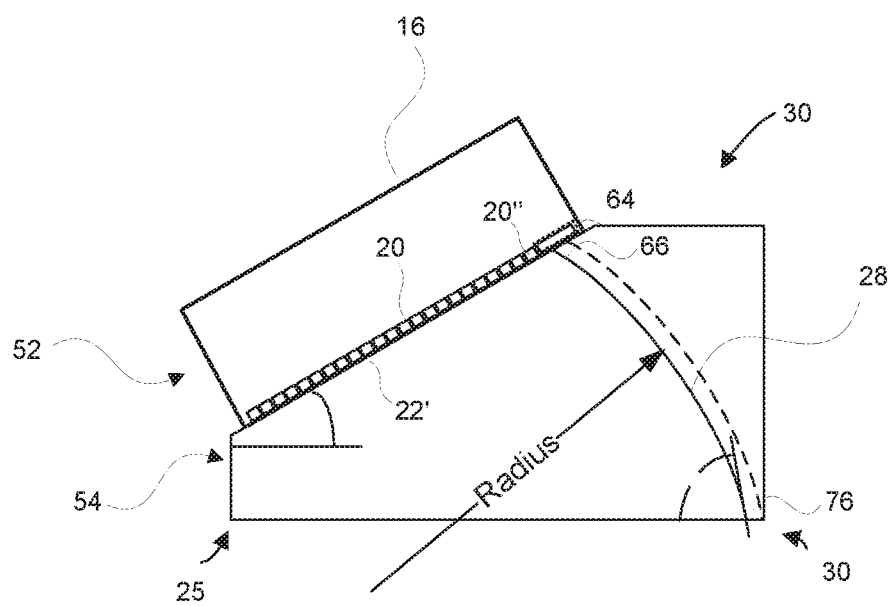
FIG. 3 is a schematic side view of a search unit, in accordance with an embodiment.

FIG. 3 is a side view of an example of the PA probe 52 and of the wedge 54. As depicted, the acoustic damping junction 28 has a curved damping profile grooved from the bottom portion of the wedge toward the top inclined surface 24 of the wedge 54 and toward the PA probe 52 when it is received on the probe receiving area. In an embodiment, the curved damping profile of the acoustic damping junction is chosen to correspond to a path of an acoustic beam emitted from the last active aperture 20" of the array at its maximum steering angle.

In this embodiment, the acoustic damping junction 28 has two opposites ends 66, 76 that are designed so that, at the lower end 76, angle is greater than a given value (usually greater than 90°-α, where α is the angle formed between the inclined face and the bottom portion of the wedge), and at upper end 66, the acoustic damping junction 28 covers the front portion of the probe housing 16 and the extended region 64 of the extended matching layer 22' as seen per any undesirable reflected acoustic signals propagating in the wedge 54 toward the front portion 36 of the probe housing 16. It is noted that a straight damping profile cannot always simultaneously satisfy the two above-mentioned conditions, unless a much bigger dumb element 72 is used, thus causing the PA probe 52 to be much longer.

Figure 4:
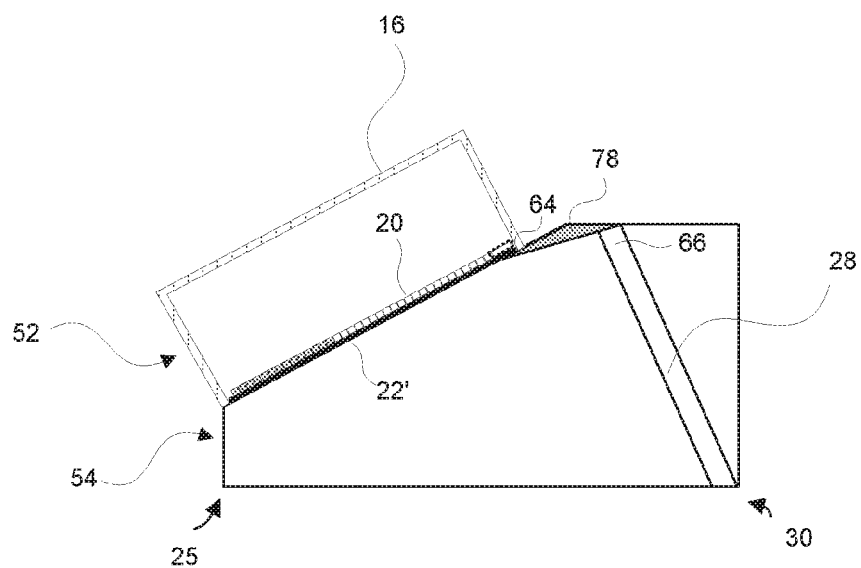
FIG. 4 is a schematic side view of a search unit, in accordance with an embodiment.

FIG. 4 is a side view of an example of the PA probe 52 and of the wedge 54. As illustrated, the wedge 54 as a damping layer 78 made of a damping material that extends between the upper band of the probe receiving area and the upper end 66 of the acoustic damping junction 28 in order to damp the acoustic discontinuities of the front portion 36 of the PA probe 52. The illustrated embodiment shows a configuration of the wedge 54 which can cause undesirable reflections toward the array 18 of transducer elements 20 but is preferred over the conventional wedge, for instance. Indeed, the damping layer 78 has a flat or curved surface which forms a given angle, e.g. 1° or 2° relative to the inclined face of the wedge in order to damp the echo signals due to the second and third interfaces. In the embodiment shown at FIG. 4, the upper end 66 of the damping junction 28 has no depth limitation as well as no angle limitation.

In an embodiment, the wedge 54 is made of a cross-linked polystyrene.

As can be understood, the examples described above and illustrated are intended to be exemplary only. The scope is indicated by the appended claims.

What is claimed is:

1. A phased-array probe to be received on a probe receiving area of a wedge, the phased-array probe comprising a probe housing, a plurality of acoustic transducer elements disposed in the probe housing and distributed along a length of a working surface of the probe housing, and a matching layer covering the plurality of acoustic transducer elements and extending to cover an extended region of the working surface of the probe housing such that the matching layer forms a closed contact with an upper end of an acoustic damping junction of the wedge when the working surface of the probe housing of the phased-array probe is received on the probe receiving area of the wedge, wherein the closed contact prevents acoustic energy from being reflected from the extended region of the working surface of the probe housing and wherein the extended region includes a spacing between a last one of the plurality of acoustic transducer elements and an interior wall of the probe housing adjacent to the last one of the plurality of acoustic transducer elements.

2. The phased-array probe of claim 1, wherein the spacing of the extended region receives an acoustic discontinuity compensator element having acoustic properties similar to that of the acoustic transducer elements.

3. The phased-array probe of claim 2, wherein the acoustic discontinuity compensator element is provided in the form of a given acoustic transducer element.

4. The phased-array probe of claim 3, wherein the given acoustic transducer element is oversized compared to each of the plurality of acoustic transducer elements.

5. The phased-array probe of claim 1, wherein the matching layer is made of a material having an impedance corresponding to that of a material of the wedge.

6. A phased-array search unit comprising:
a wedge having a base, a top inclined surface opposite to the base, the wedge tapering from a larger end to a smaller end of the wedge, the wedge further comprising an acoustic damping structure provided at an acoustic damping junction of the larger end; and
a phased-array probe having a probe housing, the housing further having a working surface to be received on the top inclined surface of the wedge; a plurality of acoustic transducer elements forming part of the working surface of the probe housing and distributed along a length of the working surface; and a matching layer covering the plurality of acoustic transducer elements along the length of the working surface of the probe housing;
wherein the matching layer and the acoustic damping structure are configured to extend toward each other to form a closed contact so that acoustic energy is substantially blocked from being transmitted beyond at least one of the matching layer and the damping junction.

7. The phased-array search unit of claim 6, wherein the acoustic damping junction extends from the base toward the top inclined surface of the wedge, the acoustic damping junction preventing the acoustic energy transmitted from the plurality of acoustic transducer elements via a reflection at the base of the wedge to be reflected back toward the plurality of acoustic transducer elements.

8. The phased-array search unit of claim 6, wherein the acoustic damping junction has an upper end being located inward from an interior wall of the probe housing and being covered by the matching layer when the working surface of the probe housing is received on the top inclined surface of the wedge.

9. The phased-array search unit of claim 6, wherein the acoustic damping junction has a plurality of spaced apart teeth, the plurality of spaced apart teeth being sized and shaped to prevent the acoustic energy from being transmitted back toward the plurality of acoustic transducer elements.

10. The phased-array search unit of claim 6, wherein the acoustic damping structure is made of a material for diffusing the acoustic energy.

11. The phased-array search unit of claim 6, wherein the matching layer extends along the length of the working surface in a direction of the larger end of the wedge when the working surface of the probe housing is received on the top inclined surface of the wedge to cover an extended region of the working surface.

12. The phased-array search unit of claim 11, wherein the extended region includes a spacing between a last one of the plurality of acoustic transducer elements and a wall of the probe housing adjacent to the last one of the plurality of acoustic transducer elements.

13. The phased-array search unit of claim 12, wherein the spacing of the extended region of the base portion receives an acoustic discontinuity compensator element, the acoustic discontinuity compensator element having acoustic properties similar to the acoustic properties of the acoustic transducer elements.

14. The phased-array search unit of claim 6, wherein the base includes a planar surface.

15. The phased-array search unit of claim 6, wherein the top inclined surface includes a planar surface and has an inclination ranging from 15° to 55° relatively to the base.

16. The phased-array search unit of claim 6, wherein the matching layer is made of a material having an impedance corresponding to that of a material of the wedge.

17. The phased-array search unit of claim 6, wherein the acoustic damping junction has a curved damping profile grooved from the base of the wedge toward the top inclined surface of the wedge.

18. The phased-array search unit of claim 6, wherein the working surface includes a planar surface.

19. The phased-array search unit of claim 6, wherein the plurality of acoustic transducer elements are spaced from one another along the length of the working surface.

* * * * *